US011317965B2

(12) United States Patent
Govari et al.

(10) Patent No.: US 11,317,965 B2
(45) Date of Patent: May 3, 2022

(54) REDUCED SIZE FORCE SENSOR

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Yehuda Algawi, Binyamina (IL); Ilya Sitnitsky, Nahariya (IL); Joseph Thomas Keyes, Glendora, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 786 days.

(21) Appl. No.: 15/452,843

(22) Filed: Mar. 8, 2017

(65) Prior Publication Data
US 2018/0256247 A1    Sep. 13, 2018

(51) Int. Cl.
| A61B 18/14 | (2006.01) |
| A61B 34/20 | (2016.01) |
| A61B 5/00 | (2006.01) |
| A61B 5/06 | (2006.01) |
| A61N 1/05 | (2006.01) |
| A61N 1/362 | (2006.01) |
| A61B 18/00 | (2006.01) |

(52) U.S. Cl.
CPC .......... *A61B 18/1492* (2013.01); *A61B 5/062* (2013.01); *A61B 5/065* (2013.01); *A61B 5/6885* (2013.01); *A61B 34/20* (2016.02); *A61N 1/0563* (2013.01); *A61N 1/362* (2013.01); *A61B 2018/00351* (2013.01); *A61B 2018/00577* (2013.01); *A61B 2018/00642* (2013.01); *A61B 2018/00791* (2013.01); *A61B 2034/2046* (2016.02)

(58) Field of Classification Search
CPC ..... A61B 5/065; A61B 5/6843; A61B 5/6885; A61B 2034/2046; A61B 18/1492; A61B 2018/00642; A61N 1/0563; A61N 1/362
See application file for complete search history.

(56) References Cited

U.S. PATENT DOCUMENTS

| 6,226,542 B1 | 5/2001 | Reisfeld |
| 6,241,724 B1 | 6/2001 | Fleischman et al. |

(Continued)

FOREIGN PATENT DOCUMENTS

| CN | 205041520 U | 2/2016 |
| JP | 2002238844 A | 8/2002 |

(Continued)

OTHER PUBLICATIONS

European Search Report dated Jun. 28, 2018 from corresponding European Patent Application No. 18160424.0.

(Continued)

*Primary Examiner* — Michael F Peffley
*Assistant Examiner* — Samantha M Good
(74) *Attorney, Agent, or Firm* — Dergosits & Noah LLP; Todd A. Noah

(57) ABSTRACT

A flexible probe has an assembly in its distal end that includes a transmitter and a receiver that receives signals from the transmitter for sensing a position of the receiver relative to the transmitter. A resilient element disposed between the transmitter and the receiver is configured to deform in response to pressure exerted on the distal tip when the distal tip engages a wall of a body cavity.

10 Claims, 8 Drawing Sheets

(56) References Cited

U.S. PATENT DOCUMENTS

| | | |
|---|---|---|
| 6,301,496 B1 | 10/2001 | Reisfeld |
| 6,695,808 B2 | 2/2004 | Tom |
| 6,814,733 B2 | 11/2004 | Schwartz et al. |
| 6,892,091 B1 | 5/2005 | Ben-Haim et al. |
| 6,915,149 B2 | 7/2005 | Ben-Haim |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 9,204,820 B2 | 12/2015 | Clark et al. |
| 2005/0267332 A1 | 12/2005 | Paul et al. |
| 2007/0100332 A1 | 5/2007 | Paul et al. |
| 2009/0093806 A1 | 4/2009 | Govari et al. |
| 2009/0099551 A1 | 4/2009 | Tung et al. |
| 2011/0130648 A1 | 6/2011 | Beeckler et al. |
| 2013/0102868 A1 | 4/2013 | Fandrey et al. |
| 2014/0018665 A1 | 1/2014 | Meredith et al. |
| 2014/0187917 A1 | 7/2014 | Clark et al. |
| 2014/0276006 A1 | 9/2014 | Sliwa et al. |
| 2016/0228180 A1 | 8/2016 | Sliwa et al. |
| 2017/0027476 A1* | 2/2017 | Kariv .................... A61B 5/065 |
| 2017/0055873 A1* | 3/2017 | Clark .................. A61B 5/6885 |

FOREIGN PATENT DOCUMENTS

| | | |
|---|---|---|
| JP | 2014-128676 A | 7/2014 |
| JP | 2014-128680 A | 7/2014 |
| JP | 2016-536065 A | 11/2016 |
| WO | 96/05768 A1 | 2/1996 |

OTHER PUBLICATIONS

Pending U.S. Appl. No. 14/974,731, filed Dec. 18, 2015.
Pending U.S. Appl. No. 15/347,242, filed Nov. 9, 2016.
Ataollahi, Asghar et al., "Novel Force Sensing Approach Employing Prismatic-Tip Optical Fiber Inside an Orthoplanar Spring Structure", IEEE/ASME Tranactions on Mechatronics, Feb. 2014, pp. 121-130, vol. 19 No. 1.
Search Report from corresponding Japanese Patent Application No. 2018-040493, dated Oct. 15, 2021.

* cited by examiner

REDUCED SIZE FORCE SENSOR

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for diagnostic and surgical purposes. More particularly, this invention relates to measurements of force, pressure or mechanical tension or compression using catheters for diagnostic and surgical procedures in the heart.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

Commonly assigned U.S. Patent Application Publication No. 2009/0093806 to Govari et al., which is herein incorporated by reference, describes another application of contact pressure measurement, in which deformation in response to pressure on a resilient member located at the distal end of a catheter is measured using a sensor.

SUMMARY OF THE INVENTION

There is provided according to embodiments of the invention a flexible probe that is adapted for insertion into a body cavity of a living subject. The probe has an assembly in its distal end that includes a transmitter and a receiver that receives signals from the transmitter for sensing a position of the receiver relative to the transmitter. A resilient element disposed between the transmitter and the receiver is configured to deform in response to pressure exerted on the distal tip when the distal tip engages a wall of the body cavity.

According to an aspect of the apparatus, the transmitter includes a single coil. There may be a high permeability core disposed in the coil.

According to another aspect of the apparatus, the receiver has three coils. There may be respective high permeability cores disposed in the three coils.

According to a further aspect of the apparatus, the assembly also includes a plurality of localizer coils that are operative to respond to incident radio-frequency radiation from an external source, the localizer coils is integrated as part of a receiver coil circuitry.

According to another aspect of the apparatus, the resilient element is a nitinol spring.

According to still another aspect of the apparatus, the resilient element is a tubular segment of an elastic material having a plurality of helical cuts formed therethrough.

According to a further aspect of the apparatus, the resilient element is a single coil spring, which can be a nitinol spring.

According to one aspect of the apparatus, the single coil spring has gaps occupied by a permeable material.

According to an additional aspect of the apparatus, the assembly includes a heat-resistant flexible plastic sheath that covers the resilient element.

There is further provided according to embodiments of the invention a method, which is carried out by providing a flexible probe that is adapted for insertion into a body cavity of a living subject. An assembly in the distal end of the probe includes a transmitter, a receiver and a resilient element disposed between the transmitter and the receiver. The method is further carried out by deforming the resilient element by exerting pressure on the distal tip when the distal tip engages a wall of the body cavity, and while deforming the resilient element emitting signals from the transmitter, receiving the signals in the receiver and processing the signals to determine a position of the receiver relative to the transmitter.

According to an aspect of the method, processing the signals includes calculating the position of the receiver relative to the transmitter responsively to an amplitude of the signals.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

System Overview

Figure 1:
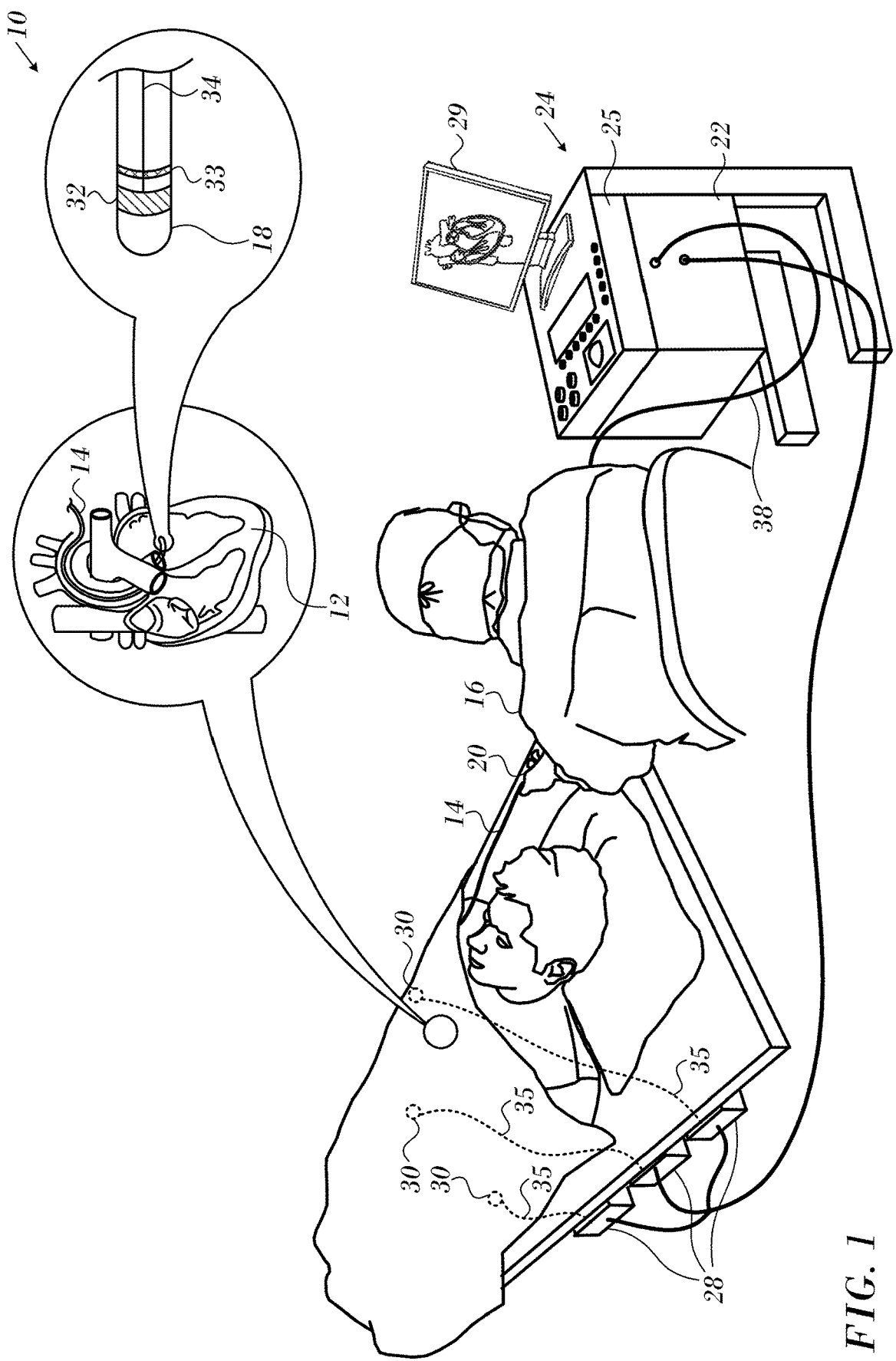
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, cryogenic energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

First Embodiment

Figure 2:
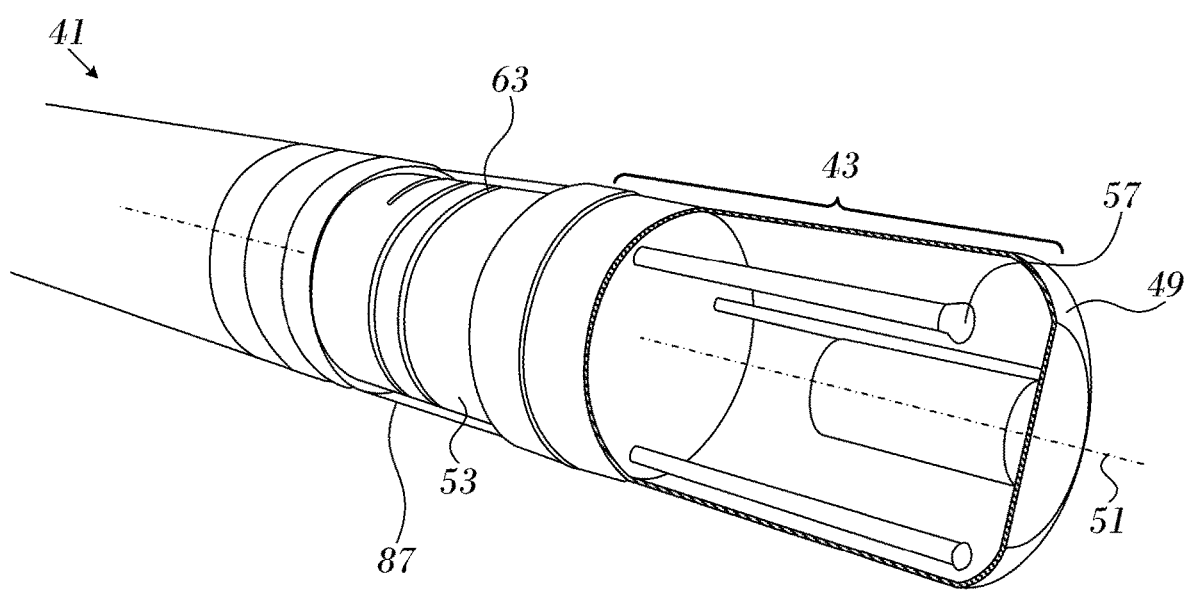
FIG. 2 is a partially cut-away view of distal portion of a catheter in accordance with an embodiment of the invention.
Figure 3:
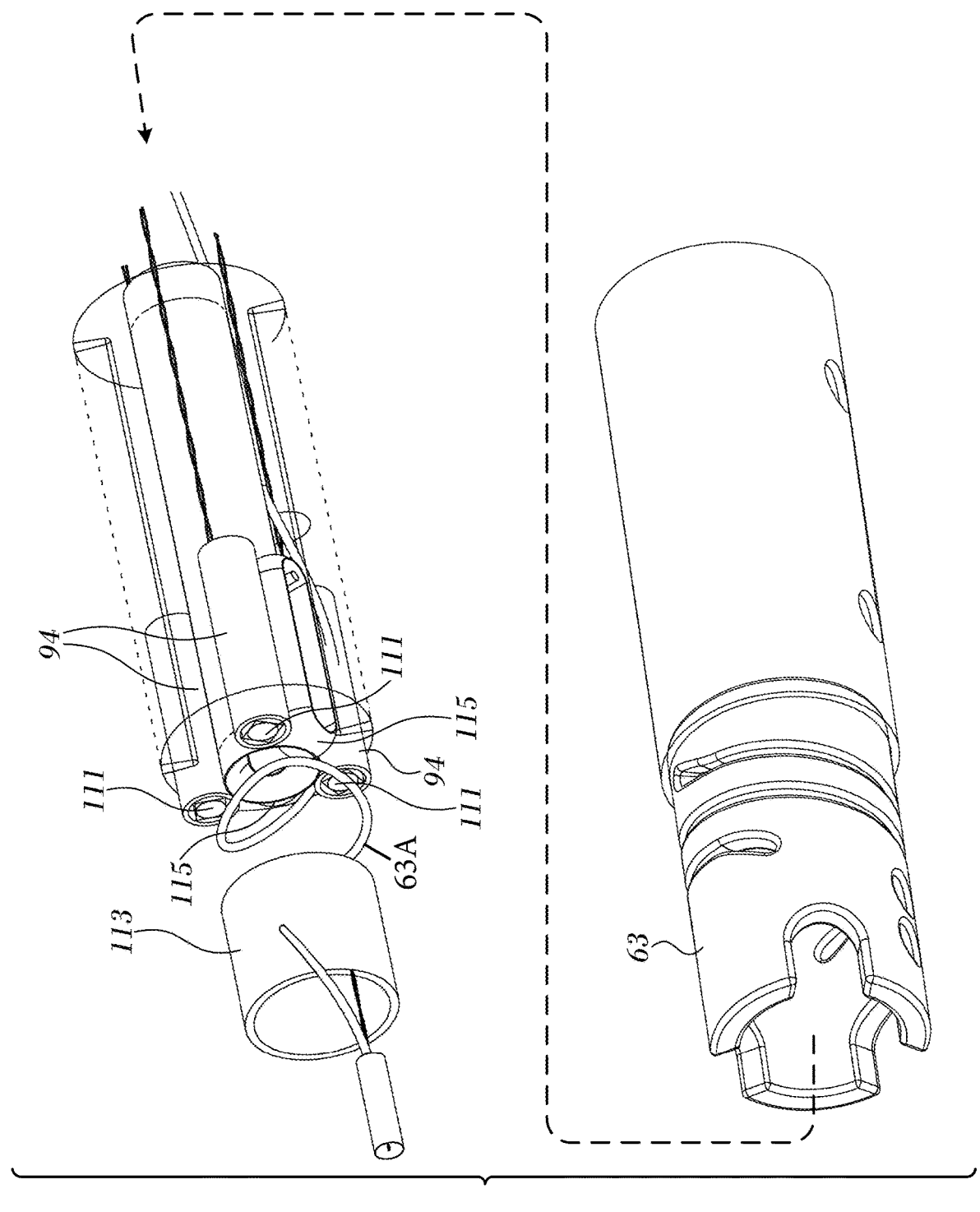
FIG. 3 is a subassembly suitable for use in the catheter shown in FIG. 2 in accordance with an embodiment of the invention.

Reference is now made to FIG. 2 and to FIG. 3, which are respectively a partially cut-away view of distal portion 41 of a catheter and a schematic, partially exploded view an assembly 109 in the distal portion 41 in accordance with embodiments of the invention. As shown in FIG. 2, the distal portion 41 has an ablation electrode 43. A temperature sensor 57 may be present in the distal portion 41 to monitor temperatures at the ablation site. A flexible spring, helix 63, is a tubular piece of an elastic material having a plurality of intertwined helical cuts therethrough along a portion of a length of the piece, which contracts and expands along axis of symmetry 51 as the contact force between the catheter and tissue varies.

Contact force sensor 53, which includes the helix 63, is disposed in the distal portion proximal to the ablation electrode 43. The contact force sensor 53 comprises by a radiofrequency receiver—transmitter combination (not shown in FIG. 2). In this embodiment the receiver is proximal to the transmitter. However, they may be disposed in the opposite order. The contact force sensor 53 forms a deformable coupling member within the distal portion 41. The two part implementation simplifies assembly of a magnetic field generator and magnetic position sensor into the member.

The assembly 109 is typically covered by a flexible plastic sheath 87. When catheter 69 is used, for example, in ablating endocardial tissue by delivering radio-frequency electrical energy through electrode 89, considerable heat is generated in the area of distal tip 49. For this reason, it is desirable that plastic sheath 87 comprises a heat-resistant plastic material, such as polyurethane, whose shape and elasticity are not substantially affected by exposure to the heat. Most importantly, plastic sheath 87 serves to keep blood out of the interior of the catheter.

As best appreciated in FIG. 3, the contact force sensor 53 comprises a paired radiofrequency transmitter and receiver. The receiver is a set of three coils 94, optionally provided with internal ferrite cores 111 for signal enhancement. The coils 94 face a transmitting coil 113, which is a single frequency loop antenna that emits radiofrequency signals that are received in the coils 94. The three coils 94 generate signals from the incident radiofrequency radiation produced by transmitting coil 113. The amplitude of the received radiofrequency signals varies generally inversely with the distance between the coils 94 and the transmitting coil 113, and thus provides a measure of the contact force-dependent deformation of the helix 63. As illustrated in FIG. 3, a single coil 63A resilient member is disposed between the transmitting coil 113 and the receiver coils 94. As will be seen from the description of the embodiments below, the transmitter and the receiver can be implemented respectively as planar printed circuit boards (PCBs). This reduces the overall size of the contact force sensor 53.

The assembly 109 comprises localizer coils 115 that function as a location detector by generating position-dependent signals from incident RF radiation produced by external field generating coils 28 (FIG. 1). The field generating coils 28 (typically nine) are fixed in a location pad that is positioned beneath a patient. The localizer coils 115 are circumscribed by the three coils 94.

In some embodiments the signals received in the three coils 94 may be distinguished by using different frequencies in the transmitting coil 113. Analysis of the force-dependent signals gives the magnitude of the force on the distal tip. The analysis may also reveal the orientation of the distal tip with respect to the axis of the proximal end of the helix 63, i.e., the amount of bending of the helix 63 about axis of symmetry 51.

A fuller description of a force sensor using these components is given in PCT Patent Document WO96/05768 of Ben Haim, commonly assigned U.S. Patent Application Publications No. 2011/0130648 and 2009/0093806 and commonly assigned application Ser. No. 14/974,731, which are herein incorporated by reference.

Figure 4:
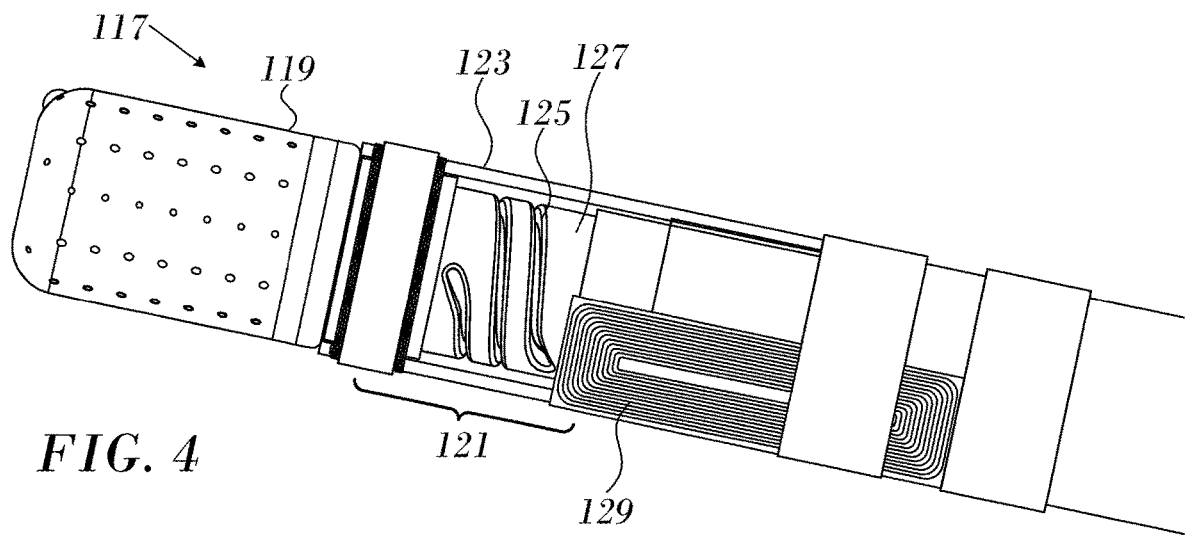
FIG. 4 is an elevation of the distal portion of a cardiac catheter in accordance with an embodiment of the invention.

Reference is now made to FIG. 4, which is an elevation of the distal portion of a cardiac catheter 117 in accordance with an embodiment of the invention. The catheter 117 has an ablation electrode 119 at its distal end, and a resilient contact force sensor assembly 121 that includes a contact force sensor. Visible are a plastic sheath 123 that extends to the proximal portion of the ablation electrode 119. Helical spring 125 is formed as a cut-out in tubular plastic material 127. A localizer coil 129 is disposed proximal to the spring 125. The transmitter and receiver shown in FIG. 3 are present, but not seen in FIG. 4.

Second Embodiment

Figure 5:
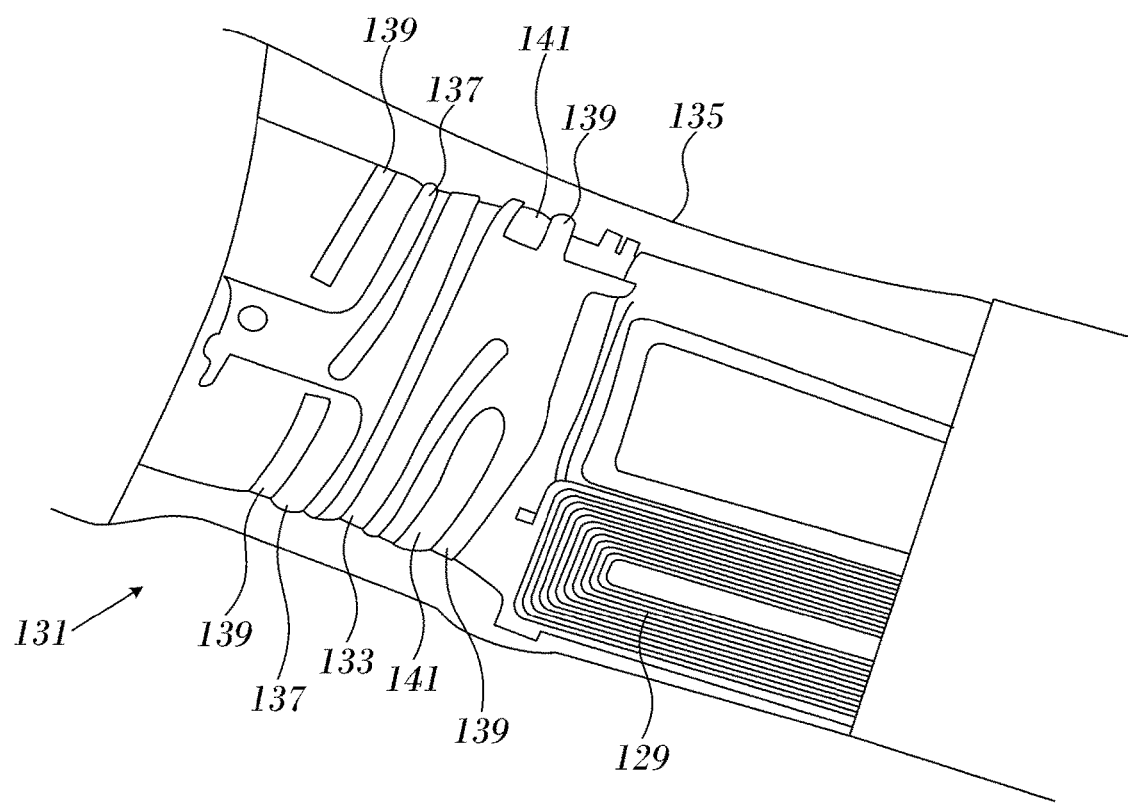
FIG. 5 is a magnified elevation of an assembly in the distal portion of a cardiac catheter in accordance with an alternate embodiment of the invention.

Reference is now made to FIG. 5, which is a magnified view of an assembly 131 in the distal portion of a cardiac catheter in accordance with an alternate embodiment of the invention. The assembly 131 is similar to the assembly 121 (FIG. 3), except now a nitinol spring 133 is employed in the contact force sensor. Plastic sheath 135 covers the spring 133. The spring 133 slides with respect to the sheath 135. The inner diameter of the sheath 135 is larger than the outer diameter of the spring 133. Edges of the receiving coils 137 and transmitting coils 141 are seen beneath the spring 133. A magnetically permeable material 139 resides on top of both transmitting and receiving coils.

Third Embodiment

Figure 6:
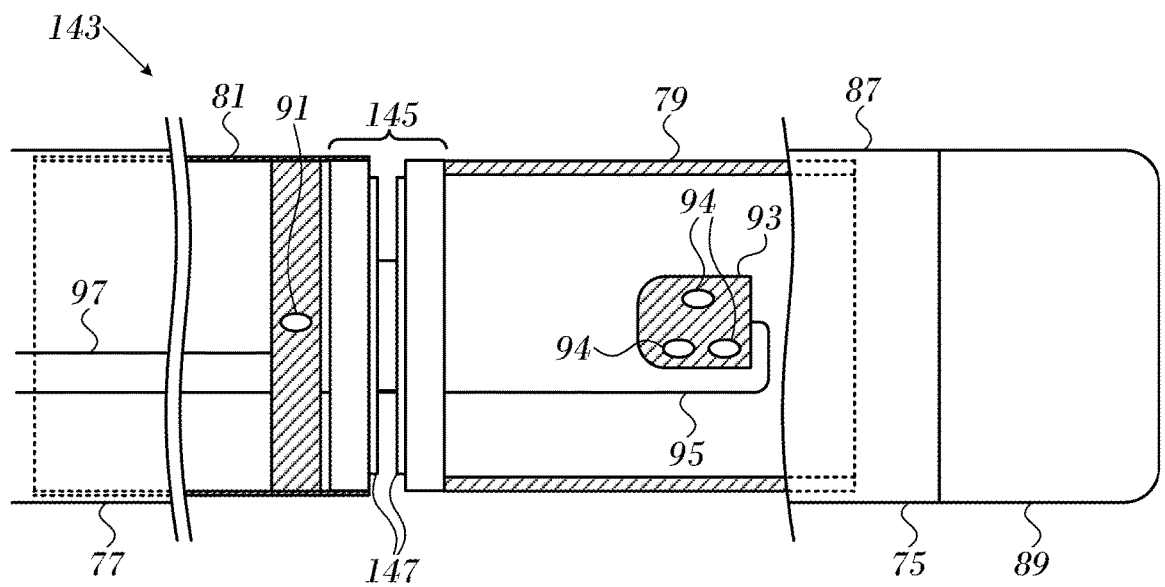
FIG. 6 is a schematic sectional view of the distal end of a catheter in accordance with an alternate embodiment of the invention.

Reference is now made to FIG. 6, which is a schematic sectional view of the distal end of a catheter 143 in accordance with an alternate embodiment of the invention. In this embodiment an assembly 145 contains two flat spring coils 147. Typically the assembly 145 has a diameter of 2.5 mm and a length of 1 mm. Transmitter 91 and receiving coils 94 of receiver 93 are disposed on opposite sides of the assembly 145, and may comprise printed circuit boards. Conductors 95, 97 supply the transmitter 91 and receiver 93.

Figure 7:
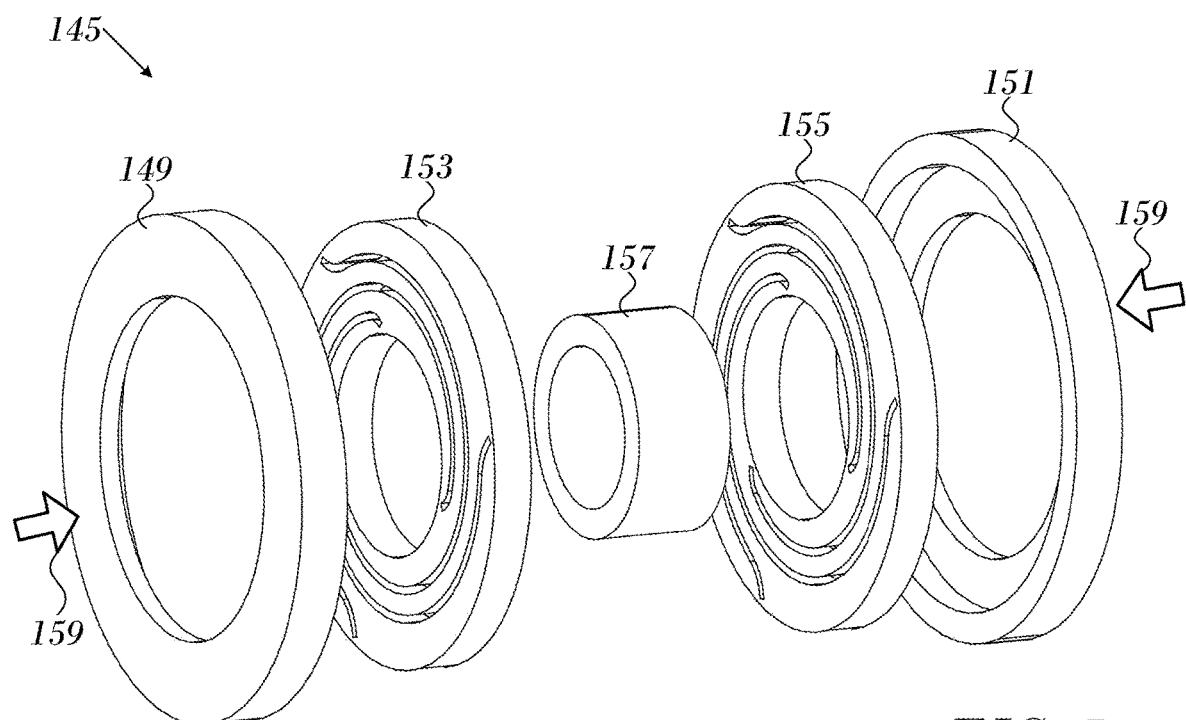
FIG. 7 is an exploded view of the assembly shown in FIG. 6 in slight perspective in accordance with an embodiment of the invention.

Reference is now made to FIG. 7, which is an exploded view of the assembly 145 (FIG. 5) shown in slight perspective in accordance with an embodiment of the invention. The assembly 145 has a transmitter retainer 149 and a receiver retainer 151. The transmitter 91 and receiver 93 (not shown in FIG. 6) may be attached to these retainers. The transmitter retainer 149 and receiver retainer 151 respectively mate with external edges of a first flat spring coil 153 and a second flat spring coil 155. The flat spring coils 153, 155 are held apart by a spacer 157, which mates with internal edges of the flat spring coils 153, 155. The flat spring coils 153, 155 deform in response to a compressive force that urge the transmitter retainer 149 and the receiver retainer 151 toward one another as indicated by arrows 159 in FIG. 6. The flat spring coils 153, 155 return to a resting state when the compressive force is removed.

The flat spring coils 153, 155 can be mass produced to reduce unit cost. The designs can be cut, stamped, or otherwise formed from planar sheet metal such as flat nitinol sheet and may be shape-set into their final forms. Minimizing thickness of the elastic portion of the spring is important in cardiac catheters, as the transmitter retainer 149 and receiver retainer 151 are at opposite ends of the contact force sensor, separating the transmitter 91 and receiver 93. (FIG. 5). The transmitter 91 and receiver 93 are separated by a distance in the range of 0.1-1.5 mm. Moreover, by laser-cutting the sheet metal into a pattern, no welds are necessary, which keeps unit cost low, as well as improving reliability relative to conventional welded springs.

Further details of techniques for manufacturing spring coils that are suitable, mutatis mutandis, for the flat spring coils 153, 155 are disclosed in commonly assigned, copending application Ser. No. 15/347,242, entitled "Coils Formed in Folded Nitinol Sheet", whose disclosure is herein incorporated by reference.

As in the previous embodiment, the assembly 145, the transmitter 91 and the receiver 93 may be constructed as an integral module with an electrical connection between the transmit and receive section.

Fourth Embodiment

Figure 8:
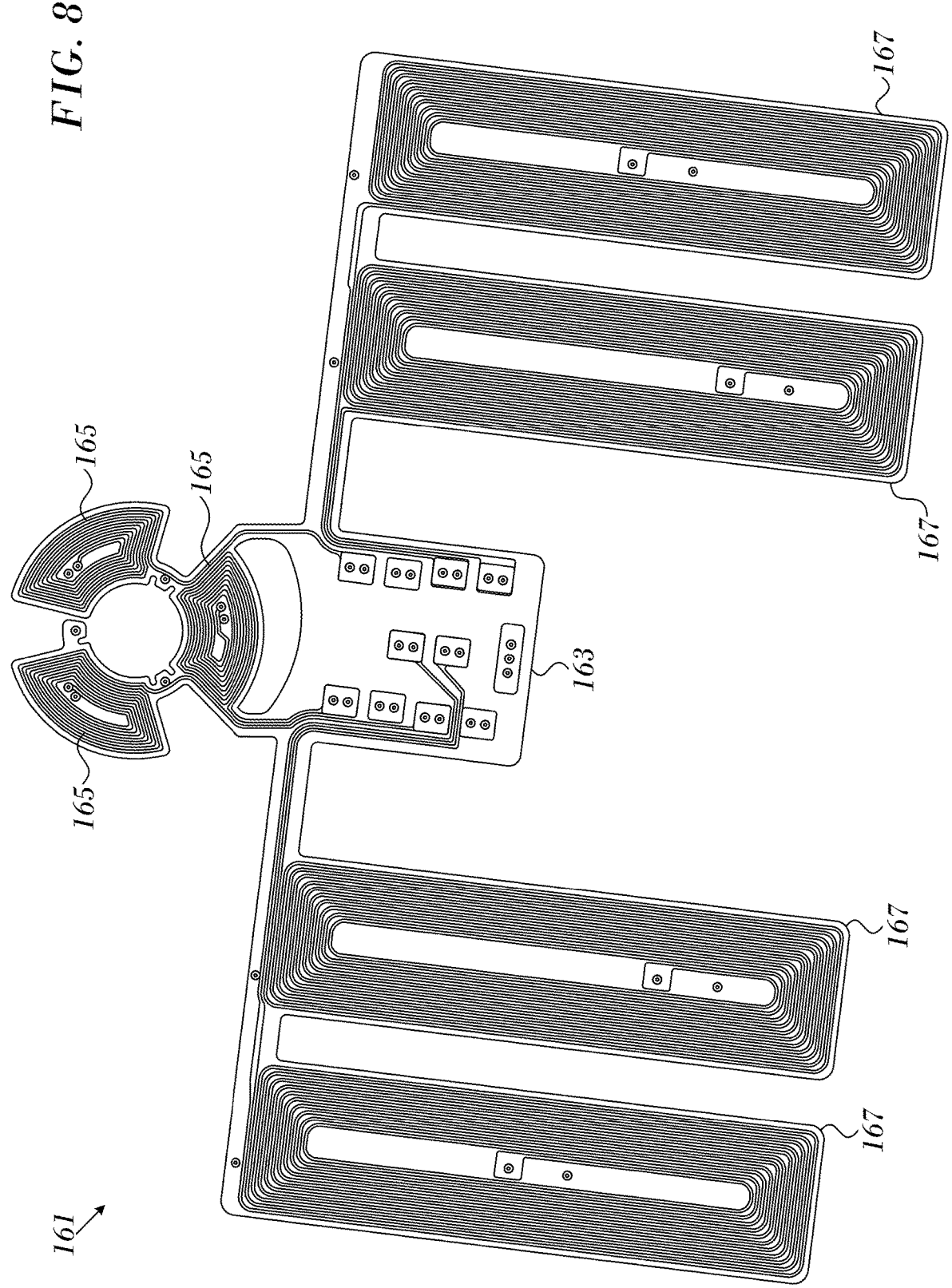
FIG. 8, which is top view of a planar assembly of a contact force sensor with integrated location coils in accordance with an embodiment of the invention.

In this embodiment, the transmitter and receiver are planar structures attached to opposite ends of a flat spring coil. The distance between the transmitter and receiver varies as the spring coil deforms and relaxes. Reference is now made to FIG. 8, which is top view of a planar assembly 161 in a contact force sensor with integrated location coils in accordance with an embodiment of the invention. The assembly 161 can be mounted at either end of a flat spring coil (not shown), and has electronic circuitry 163 arranged formed as a circuit board, and configured as a transmitter or a receiver. The circuit board can be covered with a material having high magnetic permeability in order to improve magnetic alignment. The material can be mu-metal, for example, in the form of trapezoids that conform to the shape of the circuit board. The electronic circuitry 163 that is connected to three coils 165 circularly arranged at 120 degree angles. In this example the coils 165 are used as receiving coils.

The arrangement for transmitting coils is similar. When the coils 165 are used as transmitting coils, the transmitter comprises three individual transmitters. From the description below, it will be seen that the transmitting coils align with respective receiving coils, which increases the accuracy of the readings of the contact force sensor. The three transmitting coils may be connected so that they are either in series and can be powered with one AC generator or are in parallel where they can be run at different frequencies by different AC generators.

Also shown are optional windings 167. The windings 167 are components of the positioning sub-system noted in FIG. 1, which is outside the scope of this disclosure.

Figure 9:
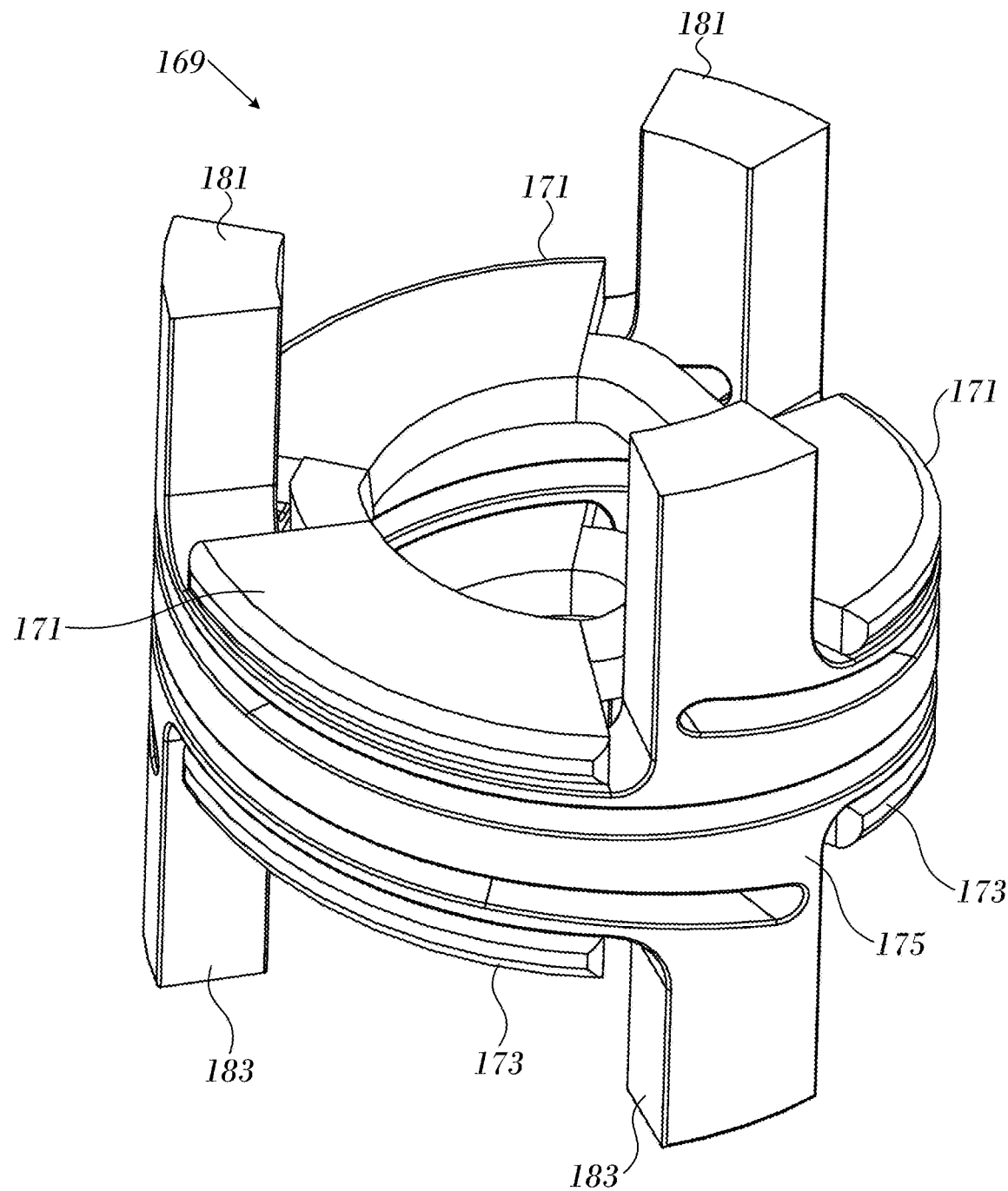
FIG. 9, which is an oblique view of a spring assembly in accordance with an embodiment of the invention.

Reference is now made to FIG. 9, which is an oblique view of a spring assembly 169 in accordance with an embodiment of the invention. Three planar transmitting coils 171 oppose receiving coils 173 on opposite ends of a compressible spring 175 arranged as in a helix having at least three windings and flat surfaces.

Figure 10:
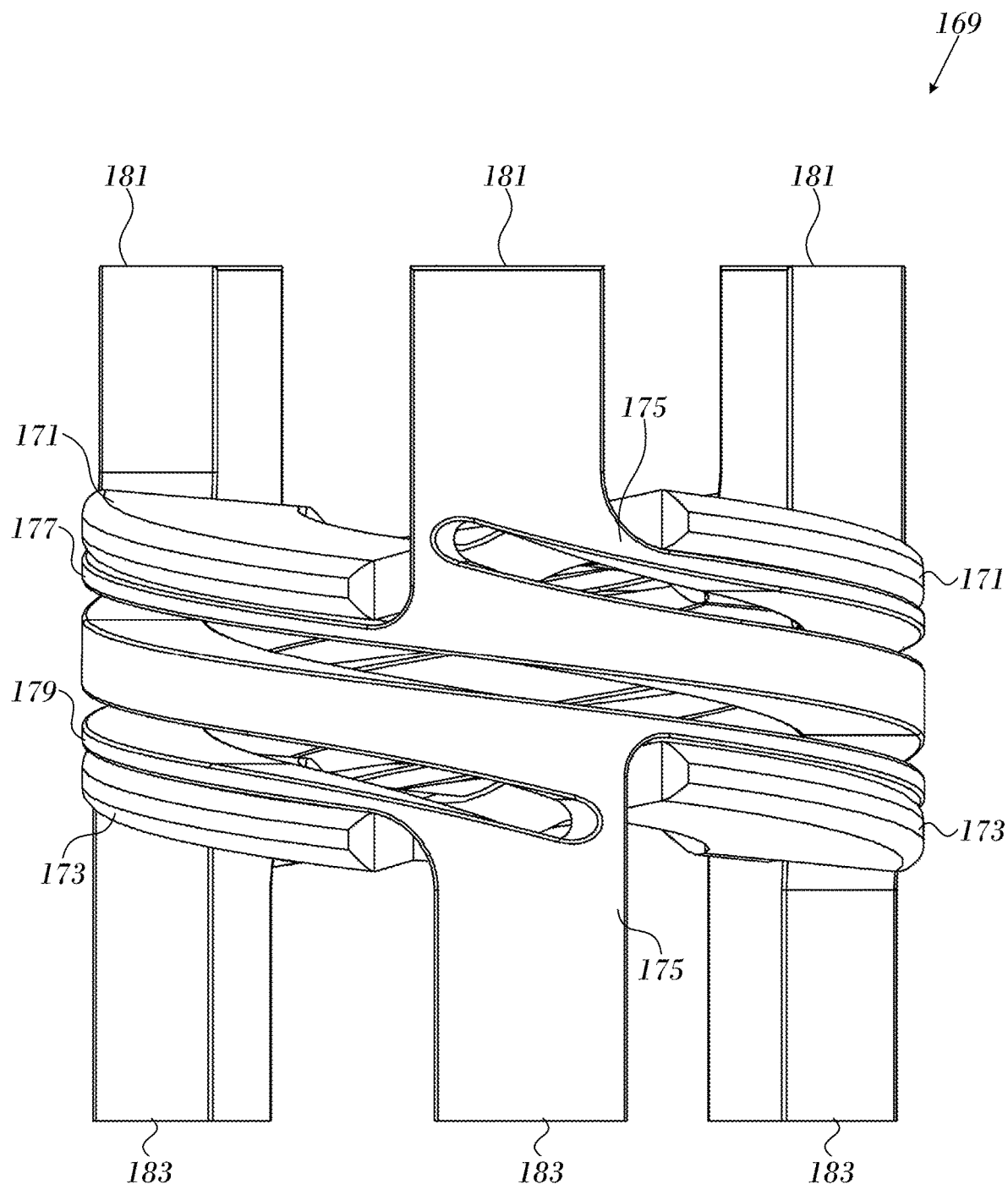
FIG. 10 is a side elevation of the assembly shown in in FIG. 9 in accordance with an embodiment of the invention.

Reference is now made to FIG. 10, which is a side elevation of the assembly 169 in accordance with an embodiment of the invention. The transmitting coils 171 and receiving coils 173 are flexible, and remain applied to the upper and lower flat surfaces 177, 179 of the spring 175 as the spring deforms responsively to compressive force acting against upper and lower legs 181, 183. The terms "upper" and "lower" are used arbitrarily herein to distinguish opposite directions. These terms have no physical meanings with respect to the actual configuration of the assembly 169.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A reduced size contact force sensor apparatus, comprising:
    a flexible probe having a proximal portion and a distal end, the probe adapted for insertion into a body cavity of a living subject, the probe having a distal tip comprising an electrode at the distal end of the probe; and
    an assembly in the distal end of the probe, comprising:
        a flexible spring disposed in the distal end proximal to the electrode, the flexible spring having a plurality of intertwined helical cuts therethrough along a portion of a length of the spring, the flexible spring being configured to deform in response to pressure exerted on the distal tip when the distal tip engages a wall of the body cavity;

a transmitter disposed within the flexible spring;

a receiver disposed within the flexible spring configured to receive signals from the transmitter for sensing a position of the receiver relative to the transmitter; and a single coil spring disposed within the flexible spring between the transmitter and the receiver, the single coil spring being configured to deform commensurate with the flexible spring in response to pressure exerted on the distal tip when the distal tip engages a wall of the body cavity and reduce the distance between the transmitter and the receiver as the flexible spring and single coil spring deform.

2. The apparatus according to claim 1, wherein the transmitter comprises a single coil.

3. The apparatus according to claim 2, wherein the transmitter further comprises a high permeability core disposed in the coil.

4. The apparatus according to claim 1, wherein the receiver comprises three coils.

5. The apparatus according to claim 4, wherein the receiver further comprises respective high permeability cores disposed in the three coils.

6. The apparatus according to claim 4, wherein the assembly further comprises a plurality of localizer coils that are operative to respond to incident radiofrequency radiation from an external source, the localizer coils being integrated as part of a receiver coil circuitry.

7. The apparatus according to claim 1, wherein the assembly further comprises a heat-resistant flexible plastic sheath.

8. A method comprising the steps of: providing a flexible probe having a proximal portion and a distal end, the probe adapted for insertion into a body cavity of a living subject, the probe having a distal tip comprising an electrode at the distal end of the probe; providing an assembly in the distal end of the probe, comprising: a flexible spring disposed in the distal end proximal to the electrode, the flexible spring having a plurality of intertwined helical cuts therethrough along a portion of a length of the spring, a transmitter disposed within the flexible spring, a receiver disposed within the flexible spring configured to receive signals from the transmitter for sensing a position of the receiver relative to the transmitter, and a single coil spring disposed within the flexible spring between the transmitter and the receiver, the single coil spring being configured to deform commensurate with the flexible spring in response to pressure exerted on the distal tip when the distal tip engages a wall of the body cavity and reduce the distance between the transmitter and the receiver as the flexible spring and single coil spring deform, and; deforming the flexible spring by exerting pressure on the distal tip when the distal tip engages a wall of the body cavity; during the deforming of the flexible spring: emitting signals from the transmitter; receiving the signals in the receiver and processing the signals to determine a position of the receiver relative to the transmitter.

9. The method according to claim 8, wherein processing the signals comprises calculating the position of the receiver relative to the transmitter responsively to an amplitude of the signals.

10. The method according to claim 8, further comprising covering the assembly with a heat-resistant flexible plastic sheath.

\* \* \* \* \*